(12) United States Patent
Wilson et al.

(10) Patent No.: US 6,867,227 B2
(45) Date of Patent: Mar. 15, 2005

(54) COMPOUNDS THAT EXHIBIT SPECIFIC MOLECULAR RECOGNITION OF MIXED NUCLEIC ACID SEQUENCES AND BIND THE DNA MINOR GROOVE AS A DIMER

(75) Inventors: W. David Wilson, Atlanta, GA (US); David W. Boykin, Atlanta, GA (US); Richard R. Tidwell, Pittsboro, NC (US)

(73) Assignees: The University of North Carolina at Chapel Hill, Chapel Hill, NC (US); Georgia State University Research Foundation, Inc., Atlanta, GA (US)

(*) Notice: Subject to any disclaimer, the term of this patent is extended or adjusted under 35 U.S.C. 154(b) by 0 days.

(21) Appl. No.: 10/653,677

(22) Filed: Sep. 2, 2003

(65) Prior Publication Data

US 2004/0053981 A1 Mar. 18, 2004

Related U.S. Application Data (62) Division of application No. 09/745,004, filed on Dec. 20, 2000, now Pat. No. 6,613,787.
(60) Provisional application No. 60/172,863, filed on Dec. 20, 1999.

(51) Int. Cl.[7] .................. A61K 31/423; A61K 31/4184; C07D 235/15; C07D 263/57; C07D 413/04
(52) U.S. Cl. ....................... 514/375; 514/394; 548/224; 548/304.7
(58) Field of Search ................................. 514/375, 394; 548/224, 304.7

(56) References Cited

U.S. PATENT DOCUMENTS 5,723,288 A  3/1998  Dykstra et al. ................ 435/6

FOREIGN PATENT DOCUMENTS

WO    WO 9640997 A    12/1996    ............ C12Q/1/68

OTHER PUBLICATIONS

International Search Report for PCT/US00/34794, Apr. 27, 2001.

K.T. Hopkins et al., Extended aromatic furan derivatives as Anti–*Pneumocystis carinii* Agents, *Journal of Medicinal Chemistry* 41, 3872–3878 (1998).

D.W. Boykin et al., 2, 5–Bis[4–(N–alkylamidino)phenyl] furans as Anti–*Pneumocystis carinii* Agents, *J. Med. Chem.* 41, 124–129 (1998).

J.L. Seifert et al., Spontaneous assembly of helical cyanine dye aggregates on DNA nanotemplates, *J. Am. Chem. Soc.* 121, 2987–2995 (1995).

L. Wang et al., Specific molecular recognition of mixed nucleic acid sequences: an aAromatic dication thatbinds in the DNA minor groove as a dimer, *Procs. Natl. Acad. Sci.* 97, 12–16 (2000).

*Primary Examiner*—Taofiq Solola
(74) *Attorney, Agent, or Firm*—Jenkins, Wilson & Taylor, P.A.

(57) ABSTRACT

Asymmetric derivatives of furamidines with one of the phenyl rings of furamidine replaced with a benzimidazole have been found by quantitative footprinting analyses to bind GC containing sites on DNA more strongly than to pure AT sequences. These compounds have been shown to bind in the minor groove at specific GC containing sequences of DNA in a highly cooperative manner as a stacked dimer. Compounds of the present invention find use in selectively binding mixed sequence DNA, and may also be used in methods of regulating gene expression, methods of treating opportunistic infections and cancer, as well as in methods of detecting certain sequences of DNA.

4 Claims, 6 Drawing Sheets

SEQUENCE LISTING

<160> NUMBER OF SEQ ID NOS: 7

<210> SEQ ID NO 1
<211> LENGTH: 10
<212> TYPE: DNA
<213> ORGANISM: Artificial
<220> FEATURE:
<223> OTHER INFORMATION: Top strand of self-annealing oligo 1

<400> SEQUENCE: 1
cgaattcgtc                                                          10

<210> SEQ ID NO 2
<211> LENGTH: 10

```
<212> TYPE: DNA
<213> ORGANISM: Artificial
<220> FEATURE:
<223> OTHER INFORMATION: Bottom strand of self-annealing oligo 1

<400> SEQUENCE: 2
tccgaattcg                                                            10

<210> SEQ ID NO 3
<211> LENGTH: 9
<212> TYPE: DNA
<213> ORGANISM: Artificial
<220> FEATURE:
<223> OTHER INFORMATION: Top strand of self-annealing oligo 2-1

<400> SEQUENCE: 3 ctatgactc                                                              9

<210> SEQ ID NO 4
<211> LENGTH: 9
<212> TYPE: DNA
<213> ORGANISM: Artificial
<220> FEATURE:
<223> OTHER INFORMATION: Bottom strand of self-annealing oligo 2-1

<400> SEQUENCE: 4 tcgtcatag                                                              9

<210> SEQ ID NO 5
<211> LENGTH: 9
<212> TYPE: DNA
<213> ORGANISM: Artificial
<220> FEATURE:
<223> OTHER INFORMATION: Top strand of self-annealing oligo 2-2

<400> SEQUENCE: 5 ccatgattc                                                              9

<210> SEQ ID NO 6
<211> LENGTH: 9
<212> TYPE: DNA
<213> ORGANISM: Artificial
<220> FEATURE:
<223> OTHER INFORMATION: Bottom strand of self-annealing oligo 2-2

<400> SEQUENCE: 6 tcatcatgg                                                              9

<210> SEQ ID NO 7
<211> LENGTH: 271
<212> TYPE: DNA
<213> ORGANISM: Artificial
<220> FEATURE:
<223> OTHER INFORMATION: EcrRi-PvuII fragment from plasmid pBS+,
      antisense strand

<400> SEQUENCE: 7
cagctggcac gacaggtttc ccgactggaa agcgggcagt gagcgcaacg caattaatgt      60
gagttacctc actcattagg cacccaggc tttacacttt atgcttccgg ctcgtatgtt     120
gtgtggaatt gtgagcggat aacaatttca cacaggaaac agctatgacc atgattacgc    180
caagctcgga attaaccctc actaaaggga acaaaagctt gcatgcctgc aggtcgactc    240
tagaggatcc ccgggtaccg agctcgaatt c                                    271
```

COMPOUNDS THAT EXHIBIT SPECIFIC MOLECULAR RECOGNITION OF MIXED NUCLEIC ACID SEQUENCES AND BIND THE DNA MINOR GROOVE AS A DIMER

RELATED APPLICATIONS

This application is a divisional application of U.S. application Ser. No. 09/745,004 filed on Dec. 20, 2000 now U.S. Pat. No. 6,613,787, herein incorporated by reference in its entirety, which claims benefit of U.S. Provisional Application Ser. No. 60/172,863, filed Dec. 20, 1999, which is incorporated herein by reference in its entirety

STATEMENT OF FEDERAL SUPPORT

This invention was made with United States Government support under grant number AI-33363 from the National Institutes of Health. The United States Government has certain rights to this invention.

FIELD OF THE INVENTION

This invention relates to novel compounds that recognize mixed sequences (i.e., GC as well as AT base pairs), and specifically bind the DNA minor groove through dimer formation.

BACKGROUND OF THE INVENTION

Design and discovery of molecules that can regulate gene expression in cells in a desirable and predictable manner is a central goal of research at the interface of chemistry and biology. See; e.g., Schreiber, S. L., *Bioorg. Med. Chem.* 6, 1127–1152 (1998); C. Denison and T. Kodadek, *Chem. Biol.* 5, R129–R145 (1998); A. G. Papavassiliou, *Molecular Medicine Today* 358–366 (1998); R. E. Bremer, et al., *Chem. Biol.* 5, 119–133 (1998); J. Gottesfeld et al., *Nature* 387, 202–205 (1997); H. Iida, *Current Opinion Biotechnology* 10, 29–33 (1999). The developing field of "chemical genetics" requires molecules that have the necessary selectivity to recognize target genes. See, e.g., S. Schreiber, supra, and Schreiber, S., FASEB J. 11, p.M1 (1997).

A number of aromatic diamidines have been shown to bind to the minor-groove of DNA, and to exhibit useful antimicrobial activity. Various hypotheses of the mode of antimicrobial action of the aryl amidines have been proposed. However, evidence is growing that these compounds function by complex formation with DNA and subsequent selective inhibition of DNA dependent microbial enzymes. Intervention in transcription control has been demonstrated and seems to be a plausible mode of action for structurally diverse minor groove binders. B. P. Das, et al., *J Med. Chem.* 20, 531–536 (1977); D. W. Boykin, et al., *J Med. Chem.* 36, 912–916 (1995); A. Kumar et al., *Eur. J Med. Chem.* 31, 767–773 (1996); R. J. Lombardy, et al., *J. Med. Chem.* 31, 912–916 (1996); R R. Tidwell. et al., *Antimicrob. Agents Chemother.* 37, 1713–1716 (1993); R. R. Tidwell, R. R. and C. A. Bell, "Pentamidine and Related Compounds in Treatment of *Pneumocystis carinii* Infection," in *Pneumocystis carinii*, (Marcel Decker; New York, 561–583 (1993)); D. Henderson, and L. H. Hurley, *Nature Med.* 1, 525–527 (1995); J. Mote, Jr., et al., *J. Mol. Biol.* 226, 725–737 (1994); and D. W. Boykin, et al., *J Med. Chem.* 41, 124–129 (1998).

Organic cations that bind in the DNA minor groove also have biological activities that range from anti-opportunistic infection to anticancer properties. See e.g., C. Bailly, in *Advances in DNA Sequence-Specific Agents*, Vol.3, pp. 97–156 (L. H. Hurley, Ed. JAI Press Inc., London, UK, 1998); J. A. Mountzouris and L. H. Hurley, in *Bioorganic Chemistry: Nucleic Acids*, pp. 288–323, (S. M. Hecht, Ed., Oxford Univ. Press, New York, 1996); E. Hildebrant, et al., *J. Euk Microbiol.* 45, 112 (1998); and K. Hopkins et al., *J. Med. Chem.* 41, 3872 (1998). Such compounds have provided a wealth of fundamental information about nucleic acid recognition properties, and they continue to be important models in the study of nucleic acid complexes.

The DNA minor-groove and AT sequence recognition properties of molecules of this series have been probed extensively for more than 30 years. See, e.g., C. Zimmer and U. Wahnert, *Prog. Biophys. Mol. Biol.* 47, 31 (1986); B. H. Geierstanger and D. E. Wemmer, *Annu. Rev. Biophys. Biomol. Struct.* 24, 463 (1995); W. D. Wilson, in *Nucleic Acids in Chemistry and Biology*, Chapter 8 (G. M. Blackburn and M. J. Gait, Eds., IRL Press, Oxford, U.K., 1996). The compound netropsin (see FIG. 1) was the first minor groove-binding compound crystallized with a B-form DNA, and the structure of the complex provided clear suggestions about the molecular basis for AT base pair sequence-specific recognition. M. L. Kopka, et al., *Proc. Natl. Acad. Sci.* 82, 1376 (1985). The structure of netropsin also led to the development of minor-groove binding netropsin analogs, the lexitropsins, that could specifically recognize GC base pairs and could thus have extended sequence recognition capability. See, J. W. Lown et al., *Biochemistry* 25, 7408 (1986); M. L. Kopka and T. A. Larsen, in *Nucleic Acid Targeted Drug Design*, pp. 303–374C (L. Probst and T. J. Perun, Eds., Marcel Dekker Inc., New York, 1992); and M. L. Kopka et al., *Structure* 5, 1033 (1997). Initial efforts in the design of such analogs did provide compounds with enhanced recognition of GC base pairs, but unfortunately, the specificity obtained was not significant. A breakthrough in this area occurred with the discovery that the monocationic compound distamycin (FIG. 1) could bind into the minor groove of some AT sequences of DNA as a stacked, antiparallel dimer. See J. G. Pelton and D. E. Wemmer, *Proc. Natl. Acad. Sci.* 86, 5723 (1989), and J. G. Pelton and D. E. Wemmer, *J Am. Chem. Soc.* 112, 1393 (1990).

One of the early recognition principles for AT sequences was the fact that the minor groove is narrower in AT than in GC regions, and it is perhaps the most surprising feature of the dimer complex that the minor groove in B-form DNA can readily expand to the width required for dimer binding. The expansion of the groove not only allows the dimer to bind but also provides for recognition of both strands in the duplex through complementary strand recognition by the two molecules of the dimer. Replacement of pyrrole group in distamycin by imidazole provided improved GC recognition specificity with dimer complexes and current design efforts in this system have reached a high level of success. See e.g., C. L. Kielkopf, et al., *Nature Struct. Biol.* 5, 104 (1998); S. Whiteet al., *Nature* 391, 468 (1998); C. L. Kielkopf et al., *Science* 282, 111 (1998); S. E. Swalleyet al., *J. Am. Chem. Soc* 121, 1113 (1999); and D. M. Herman, et al., *J. Am. Chem. Soc* 121, 1121 (1999). With recent incorporation of hydroxypyrole groups as a recognition unit, AT and TA as well as GC and CG base pairs can now be effectively distinguished in DNA sequences by pyrrole-imidazole polyamides related to distamycin.

The pyrrole-imidazole polyamide system is the only one of the well-known minor-groove binding motifs that has been found to form the stacked-dimer recognition unit. Even netropsin, the first minor-groove binding agent to be structurally characterized in detail and a dicationic relative of the monocation distamycin (FIG. 1), does not form a dimer recognition unit. A recent crystal structure of a 2:1 netrospin-

DNA complex found that the two netropsin molecules in the complex bound in the minor groove as tandem monomer units instead of the side-by-side dimer observed with distamycin. See e.g., X. Chen, et al., *J. Mol. Biol.* 267, 1157 (1997); X. Chen, et al, *Nucleic Acids Res.* 26, 5464 (1998); and X. Chen, et al, *Nature Struct. Biol.* 1, 169 (1994). The two charges of netropsin as well as other minor groove agents, such as the furan derivatives shown in FIG. 1, have been postulated to prevent stacked-dimer formation.

Recent evidence suggests that some monocationic cyanine dyes can form an array of stacked dimers in the DNA minor groove. See J. L. Seifert, et al., *J. Am. Chem. Soc.* (in press, 1999). There are, however, other monocationic minor-groove agents, such as Hoechst 33258 (see FIG. 1 and analogs, that apparently do not form dimer DNA recognition motifs. These results indicate that the electrostatic and stereochemical requirements for minor-groove recognition of DNA by dimers are very restrictive, and further suggest that stacked dimer formation by dications is unlikely.

SUMMARY OF THE INVENTION

The present invention is based on the inventors' surprising discovery of a new class of organic dications, based on unfused-aromatic systems, that selectively recognize mixed DNA sequences (i.e., AT as well as GC base pairs) in a manner that is very sensitive to compound structure. These are the first non-peptide compounds that have mixed-sequence recognition capability and the result is particularly promising, since similar compounds readily enter cells and have generally low toxicity. See K. Hopkins et al., *J. Med. Chem.* 41, 3872–3878 (1998). A surprising feature of this discovery is that recognition occurs through highly cooperative dimer formation at the DNA binding site, a process that has been predicted not to occur for dications. The series of compounds provides a synthetically accessible new motif for specific recognition of DNA and control of gene expression. Such compounds accordingly find use in numerous therapies and treatments, including the treatment and prevention of opportunistic infections, cancer and other diseases of cell proliferation, and disorders of genetic origin (i.e., diseases caused by mutations of DNA and the like). Additionally, certain of the compounds of the present invention are fluorescent, and thus are useful for the detection of certain specific sequences recognized by the compounds of the invention.

Accordingly, a first aspect of the present invention is a compound of Formula I:

(I)

wherein:
X is selected from the group consisting of O, S, and NH;
Y is CH or N;
A is CH or N;
B is selected from the group consisting of NH, O or S;

$R_1$ is selected from the group consisting of H, loweralkyl, halogen, oxyalkyl, oxyaryl, and oxyarylakyl;

$R_2$ and $R_9$ are each independently selected from the group consisting of H, $H_2$, hydroxy, lower alkyl, cycloalkyl, aryl, alkylaryl, alkoxyalkyl, hydroxycycloalkyl, alkoxycycloalkoxy, hydroxyalkyl, aminoalkyl and alkylaminoalkyl; and $R_3$, $R_4$, $R_{13}$ and $R_{14}$ are each independently selected from the group consisting of H, lower alkyl, alkoxyalkyl, cycloalkyl, aryl, alkylaryl, hydroxyalkyl, aminoalkyl, and alkylaminoalkyl, or $R_3$ and $R_4$ together or $R_{13}$ and $R_{14}$ together represent a $C_2$ to $C_{10}$ alkyl, hydroxyalkyl, or alkylene, or $R_3$ and $R_4$ together or $R_{13}$ and $R_{14}$ together are:

wherein n is a number from 1 to 3, and $R_{10}$ is H or $-CONHR_{11}NR_{15}R_{16}$, wherein $R_{11}$ is lower alkyl and $R_{15}$ and $R_{16}$ are each independently selected from the group consisting of H and lower alkyl;

L is selected from the group consisting of:

-continued wherein $R_5$, $R_6$, $R_7$, and $R_8$ are each individually selected from the group consisting of H, alkyl, halo, aryl, arylalkyl, aminoalkyl, aminoaryl, oxoalkyl, oxoaryl, and oxoarylalkyl; and wherein said compound of Formula I binds mixed-sequence DNA in the minor groove in a dimer formation. In a preferred embodiment of the invention, the compound of Formula I is a dication, L is:

A is N; B is NH; X is O; Y is CH; $R_1$, $R_2$, $R_4$, $R_5$, $R_6$, $R_7$, $R_8$, $R_9$ and $R_{14}$ are each H; and $R_3$ and $R_{13}$ are each $H_2$.

A second aspect of the present invention is a method of selectively binding mixed sequence DNA comprising contacting a sample of DNA with a compound of Formula I.

A third aspect of the present invention is a method of detecting mixed DNA sequences comprising contacting a sample of DNA with a fluorescent compound of Formula I, and then observing fluorescence in the sample, the observation of fluorescence indicating that mixed DNA sequences have been bound.

A fourth aspect of the invention is a pharmaceutical formulation comprising a compound of Formula I in a pharmaceutically acceptable carrier.

Additional aspects of the invention include methods of controlling gene expression, methods of treating microbial infection, methods of treating cancer and other disorders of cell proliferation, and methods of treating disorders of genetic origin (i.e., where the disease state is caused by a gene mutation or mutations).

Other aspects of the present invention include the use of an active compound as described above for the preparation of a medicament for controlling gene expression, or medicament for treating a microbial infection, or a method of treating a disorder of genetic origin in a subject in need thereof.

The foregoing and other aspects of the present invention are explained in detail in the specification set forth below.

BRIEF DESCRIPTION OF THE DRAWINGS

FIG. 1. sets forth the chemical structures for the minor-groove binding compounds netropsin, distamycin, Hoechst 33258, furamidine (DB75), DB270, and DB293. FIG. 1 also sets forth the DNA sequences for oligo1, oligo2, oligo2-1 and oligo2-2, as described herein.

As illustrated in FIG. 2A, the products of the DNase I digestion were resolved on an 8% polyacrylamide gel containing 8M urea. Drug concentrations are (lanes 1–11) 0, 0.3, 0.6, 0.9, 1.2, 1.5, 1.8, 2.1, 2.4, 2.7, 3.0 μM for DB 293 and (lanes 12–15) 0, 1, 2 and 5 μM for DB270. Tracks labeled 'G' represent dimethylsulphate-piperidine markers specific for guanines. The track labeled DNA contained no drug and no enzyme. Numbers at the right side of the gel refer to the numbering scheme of the fragment. The rectangles on the left side refer to the positions of (open box) an AT-rich and (filled box) a GC-rich binding site for DB293. FIG. 2B is a graphical illustration of footprinting plots for the binding of DB293 to (open circles) the AT site 5'-AATTAA and (filled squares) the GC-rich site 5'-ACCATG. The relative band intensity R corresponds to the ratio $I_c/I_o$ where $I_c$ is the intensity of the band at the ligand concentration c and $I_o$ is the intensity of the same band in the absence of DB293. The differential cleavage plots shown in FIG. 2C compare the susceptibility of the DNA to cutting by DNase I in the presence of (filled circles) 5 μM DB270 or (open squares) 1.5 μM DB293. Deviation of points towards the lettered sequence (negative values) corresponds to a ligand-protected site and deviation away (positive values) represents enhanced cleavage. The vertical scale is in units of $\ln(f_a)$-$\ln(f_c)$, where $f_a$ is the fractional cleavage at any bond in the presence of the drug and $f_c$ is the fractional cleavage of the same bond in the control. The results are displayed on a logarithmic scale for the sake of convenience. The rectangles below the sequence show the positions of (open box) the AT binding site and (filled box) the GC-rich site.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety.

Nucleotide sequences are presented herein by single strand only, in the 5' to 3' direction, from left to right. Nucleotides are represented herein in the manner recommended by the IUPAC-IUB Biochemical Nomenclature Commission in accordance with 37 CFR §1.822 and established usage. See, e.g., *PatentIn User Manual*, 99–102 (Nov. 1990) (U.S. Patent and Trademark Office).

Certain objects, advantages and novel features of the invention will be set forth in the description that follows, and will become apparent to those skilled in the art upon examination of the following, or may be learned with the practice of the invention.

As used herein the term "alkyl" refers to $C_{1-10}$ inclusive, linear, branched, or cyclic, saturated or unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. As used herein, the term "acyl" refers to an organic acid group wherein the —OH of the carboxyl group has been replaced with another substituent (i.e., as represented by RCO—, wherein R is an alkyl or an aryl group). As such, the term "acyl" specifically includes arylacyl groups. Specific examples of acyl groups include acetyl and benzoyl. As used herein, the term "aryl" refers to 5 and 6-membered hydrocarbon and heterocyclic aromatic rings. Specific examples of aryl groups include but are not limited to cyclopentadienyl, phenyl, furan, thiophene, pyrrole, pyran, pyridine, imidazole, isothiazole, isoxazole, pyrazole, pyrazine, pyrimidine, and the like. The term "alkoxyl" as used herein refers to $C_{1-10}$ inclusive, linear, branched, or cyclic, saturated or unsaturated oxo-hydrocarbon chains, including for example methoxy, ethoxy, propoxy, isopropoxy, butoxy, t-butoxy, and pentoxy. The term "aryloxyl" as used herein refers to phenyloxyl or hexyloxyl, and alkyl, halo, or alkoxyl substituted phenyloxyl or hexyloxyl. As used herein, the terms "substituted alkyl" and "substituted aryl" include alkyl and aryl groups, as defined herein, in which one or more atoms or functional groups of the aryl or alkyl group are replaced with another atom or functional group, including for example, halogen, aryl, alkyl, alkoxy, hydroxy, nitro, amino, alkylamino, dialkylamino, sulfate, and mercapto. The terms "halo," "halide," or "halogen" as used herein refer to fluoro, chloro, bromo, and iodo groups.

As used herein, the term "mixed sequence DNA" refers to a sequence of DNA that comprises GC base pairs and AT base pairs.

Compounds of Formula I of the present invention (hereinafter referred to as the "active compounds") are useful in binding mixed sequences of DNA, i.e., GC as well as AT base pairs. Unexpectedly, the active compounds bind in the minor groove of DNA at specific GC containing sequences in a highly cooperative manner as stacked dimers. Because of the ability of the compounds of the present invention to bind to specific and mixed sequences of DNA, they are useful in controlling gene expression by, for example, intervening in gene transcription. Accordingly, the active compounds may find pharmaceutical use in the treatment of opportunistic infections such *Pneumocystis carinii*, in the treatment of cancers and other disorders of proliferation, and in the treatment of genetic disorders caused by, for example, mutations in particular genes (e.g., cystic fibrosis, adult polycystic disease, Huntington's disease, myotonic dystrophy, neurofibromatosis, etc.). Moreover, since certain compounds of the present invention are fluorescent (i.e., DB293, shown in FIG. 1), they are useful in detecting the particular DNA sequences bound by the compounds through fluorescence detection methods known in the art.

The active compounds of the present invention may be prepared by the methods set forth in K. Hopkins et al., *J. Med. Chem.* 41,3872–3878(1998). The active compounds of the present invention may also be prepared by the methods set forth in R. Kada et al., *Collect. Czech. Chem. Comm.* 38, 1700–1704 (1973), modified as described below, the disclosure of which is also incorporated herein in its entirety. Additionally, the active compounds may be administered as pharmaceutically acceptable salts. Such salts include the gluconate, lactate, acetate, tartarate, citrate, phosphate, borate, nitrate, sulfate, and hydrochloride salts. The salts of the present invention may be prepared, in general, by reacting two equivalents of the base compound with the desired acid, in solution. After the reaction is complete, the salts are crystallized from solution by the addition of an appropriate amount of solvent in which the salt is insoluble.

As noted above, the methods of the present invention are useful for treating opportunistic microbial infections such as, for example, *P. carinii* and *Giardia lamblia*. The compounds may also be useful in treating fungal infections such as *Candida albicans, Cryptococcus neoformans, Aspergillus fumigatus, Fusarium solani*, and combinations thereof. The methods of the invention are useful for treating these conditions in that they inhibit the onset, growth, or spread of the condition, cause regression of the condition, cure the condition, or otherwise improve the general well-being of a subject afflicted with, or at risk of contracting the condition.

The compounds of the present invention are useful not only in methods for treating infections and other disorders, but also in methods of inhibiting enzymes such as topoisomerase.

Subjects to be treated by the methods of the present invention are typically human subjects, although the methods of the present invention may be useful with any suitable subject known to those skilled in the art.

As noted above, the present invention provides pharmaceutical formulations comprising the aforementioned active compounds, or pharmaceutically acceptable salts thereof, in pharmaceutically acceptable carriers for oral, intravenous, or aerosol administration as discussed in greater detail below. Also, the present invention provides such compounds or salts thereof which have been lyophilized and which may be reconstituted to form pharmaceutically acceptable formulations for administration, as by intravenous or intramuscular injection.

The therapeutically effective dosage of any specific compound, the use of which is in the scope of present invention, will vary somewhat from compound to compound, and patient to patient, and will depend upon the condition of the patient and the route of delivery. As a general proposition, a dosage from about 0.1 to about 50 mg/kg will have therapeutic efficacy, with all weights being calculated based upon the weight of the active compound, including the cases where a salt is employed. Toxicity concerns at the higher level may restrict intravenous dosages to a lower level such as up to about 10 mg/kg, with all weights being calculated based upon the weight of the active base, including the cases where a salt is employed. A dosage from about 10 mg/kg to about 50 mg/kg may be employed for oral administration. Typically, a dosage from about 0.5 mg/kg to 5 mg/kg may be employed for intramuscular injection. Preferred dosages are 1 $\mu$mol/kg to 50 $\mu$mol/kg, and more preferably 22 $\mu$mol/kg and 33 $\mu$mol/kg of the compound for intravenous or oral administration. The duration of the treatment is usually once per day for a period of two to three weeks or until the condition is essentially controlled. Lower doses given less frequently can be used prophylactically to prevent or reduce the incidence of recurrence of the infection.

In accordance with the present method, pharmaceutically active compounds as described herein, or pharmaceutically acceptable salts thereof, may be administered orally as a solid or as a liquid, or may be administered intramuscularly or intravenously as a solution, suspension, or emulsion. Alternatively, the compounds or salts may also be administered by inhalation, intravenously or intramuscularly as a liposomal suspension. When administered through inhalation the active compound or salt should be in the form of a plurality of solid particles or droplets having a particle size from about 0.5 to about 5 microns, and preferably from about 1 to about 2 microns.

The present invention also provides a pharmaceutical composition suitable for intravenous or intramuscular injection. The pharmaceutical composition comprises a compound of Formula (I) described herein, or a pharmaceutically acceptable salt thereof, in any pharmaceutically acceptable carrier. If a solution is desired, water is the carrier of choice with respect to water-soluble compounds or salts. With respect to the water-insoluble compounds or salts, an organic vehicle, such as glycerol, propylene glycol, polyethylene glycol, or mixtures thereof, may be suitable. In the latter instance, the organic vehicle may contain a substantial amount of water. The solution in either instance may then be sterilized in a suitable manner known to those in the art, and typically by filtration through a 0.22 micron filter. Subsequent to sterilization, the solution may be dispensed into appropriate receptacles, such as depyrogenated glass vials. Of course, the dispensing is preferably be done by an aseptic method. Sterilized closures may then be placed on the vials and, if desired, the vial contents may be lyophilized.

In addition to compounds of Formula (I) or their salts, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

In yet another aspect of the present invention, there is provided an injectable, stable, sterile composition comprising a compound of Formula (I), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds disclosed herein or salts thereof, may be lyophilized to produce a lyophilizate which may be reconstituted with a pharmaceutically acceptable carrier, such as water, to regenerate a liposomal suspension.

Pharmaceutical formulations are also provided which are suitable for administration as an aerosol, by inhalation. These formulations comprise a solution or suspension of a desired compound described herein or a salt thereof, or a plurality of solid particles of the compound or salt. The desired formulation may be placed in a small chamber and nebulized. Nebulization may be accomplished by compressed air or by ultrasonic energy to form a plurality of liquid droplets or solid particles comprising the compounds or salts. The liquid droplets or solid particles should have a particle size in the range of about 0.5 to about 10 microns, more preferably from about 0.5 to about 5 microns. The solid particles can be obtained by processing the solid compound or a salt thereof, in any appropriate manner known in the art, such as by micronization. Most preferably, the size of the solid particles or droplets will be from about 1 to about 2 microns. In this respect, commercial nebulizers are available to achieve this purpose. The compounds may be administered via an aerosol suspension of respirable particles in a manner set forth in U.S. Pat. No. 5,628,984, the disclosure of which is incorporated herein by reference in its entirety.

Preferably, when the pharmaceutical formulation suitable for administration as an aerosol is in the form of a liquid, the formulation will comprise a water-soluble compound or a salt thereof, in a carrier which comprises water. A surfactant may be present which lowers the surface tension of the formulation sufficiently to result in the formation of droplets within the desired size range when subjected to nebulization.

As indicated, the present invention provides both water-soluble and water-insoluble compounds and salts thereof. As used in the present specification, the term "water-soluble" is meant to define any composition which is soluble in water in an amount of about 50 mg/mL, or greater. Also, as used in the present specification, the term "water-insoluble" is meant to define any composition which has solubility in water of less than about 20 mg/mL. For certain applications, water soluble compounds or salts may be desirable whereas for other applications water-insoluble compounds or salts likewise may be desirable.

The following Examples are provided to illustrate the present invention, and should not be construed as limiting thereof.

EXAMPLE 1

Synthesis of Compounds of Formula I

2-[5(6)-Nitro-2-benzimidazoyl]-5-(4-nitrophenyl)furan was prepared according to a modified literature procedure (R. Kada et al., *Collect. Czech. Chem. Comm.* 38, 1700–1704 (1973)) by reaction of 5-(4-nitrophenyl)furfural (10 mmol) with 4-nitro-1,2-phenylenediamine (10 mmol) in a mixture of DMF (25 ml) and nitrobenzene (5 ml) at 150° C. for 22 h (under nitrogen). Cooling to room-temperature gave a suspended solid which was diluted with MeOH (30 ml), collected, and finally rinsed well with ether. Yield: 2.56 g, 73%; mp 350–351° C. dec; lit mp 348–350° C.). $^1$H NMR (DMSO-$d_6$): 7.51 (d, J=3.7 Hz, 1H), 7.57 (d, J=3.7 Hz, 1H), 7.78 (d, J=8.9 Hz, 1H), 7.94 (s, 1H), 8.14 (dd, J=8.9, 2.2 Hz, 1H), 8.17 (d, J=8.8 Hz, 2H), 8.36 (d, J=9.1 Hz, 2H), 8.47 (d, J=1.7 Hz, 1H) (benzimidazole NH not observed).

2-[5(6)-Amino-2-benzimidazoyl]-5-(4-aminophenyl) furan. To a suspension of 2-[5(6)-nitro-2-benzimidazoyl]-5-(4-nitrophenyl)furan (2.63 g, 7.5 mmol) in EtOH (100 ml) was added stannous chloride dihydrate (16.0 g, 71 mmol) and the mixture was refluxed under nitrogen with vigorous stirring for 3 hr to give a solution. After stirring at room-temperature overnight, the solution was made basic by addition of aqueous NaOH and the solids were extracted with EtOAc. After drying ($Na_2SO_4$) and filtering, the solvent was removed in vacuo and the residue was dissolved in EtOH. This solution was then diluted with water to give a greenish yellow solid which was collected and dried in the desiccator ($P_2O_5$). Yield: 0.95 g, 44%; mp 161–165° C. dec. In contrast to the bis-nitro derivative, the $^1$H NMR of this bis-amine was quite complex indicating it exists as a mixture of the two possible tautomers. The $^1$H NMR of the hydrochloride salt, prepared by dissolving a sample of the free base in HCl/EtOH followed by concentration, was less complex (DMSO-$d_6$, $D_2O$): 7.17 (d, J=8.6 Hz, 2H), 7.21 (d, J=3.7 Hz, 1H), 7.30 (dd, J=8.7, 1.9 Hz, 1H), 7.63 (d, J=1.9 Hz, 1H), 7.74 (d, J=8.6 Hz, 1H), 7.78 (d, J=3.8 Hz, 1H), 7.94 (d, J=8.6 Hz, 2H).

2-[5(6)-Guanidino-2-benzimidazoyl]-5-(4-guanidinophenyl)furan. To a chilled solution of 2-[5(6)-amino-2-benzimidazoyl]-5-(4-aminophenyl)furan (0.363 g, 1.25 mmol) and 1,3-bis(tert-butoxycarbonyl)-2-methyl-2-thiopseudourea (0.755 g, 2.60 mmol) in dry DMF (25 ml) was added triethylamine (0.78 g, 7.71 mmol) followed by mercury(II) chloride (0.78 g, 2.87 mmol) and the resulting suspension was stirred at ambient temperature for 3 days. After diluting with $CH_2Cl_2$ and filtering over Celite, the dark solution was washed well with saturated $Na_2CO_3$ solution, with water (3 times), and finally with brine. After drying ($Na_2SO_4$), the solvent was removed in vacuo and the remaining oil was diluted with MeOH to give the BOC-protected bis-guanidine as a pale green solid in two crops (0.58 g). The product was purified by reprecipitation from $CH_2Cl_2$/MeOH to give, after partial concentration, a fluffy pale green solid (0.42 g, 43%), mp>400° C. dec, with darkening >300° C.

For deprotection, a solution of the protected bis-guanidine in $CHCl_3$ (12 ml) and EtOH (10 ml) was saturated with dry HCl at 0–5° C. and allowed to stir for 2 days at room-temperature to give a orange-colored suspension. After removing the solvents in vacuo, the solid was taken up in hot EtOH (60 ml), a small amount of insoluble material was filtered off, and the solvent was again removed. After trituration with ether, the yellow solid was collected and dried in vacuo for 3 days at 50–60° C. Yield: 0.24 g, 92% (40% overall from the bis-amine). $^1$H NMR (DMSO-$d_6$): 7.24 (d, J=8.6 Hz, 1H), 7.33 (d, J=3.6 Hz, 1H), 7.38 (d, J=8.6 Hz, 2H), 7.51 (br s, 3H), 7.57 (s, 1H), 7.64 (br s, 3H), 7.68 (apparent s, 1H), 7.74 (d, J=8.6 Hz, 1H), 8.05 (d, J=8.5 Hz, 2H), 10.05 (br s, 1H), 10.19 (br s, 1H). FABMS (thioglycerol): m/z 375 (100). FABHRMS:Calcd. for $C_{19}H_{18}N_8O$ ($MH^+$): 375.1682. Found: 375.1670. Anal. Calcd for $C_{19}H_{18}N_8O.3HCl.2H_2O$: C, 43.90; H, 4.85; N, 21.56; Cl, 20.46. Found: C, 43.68; H, 4.47; N, 20.68; Cl, 20.46.

1-[(5-Bromobenzo [b]furan-2-yl]-3-dimethylaminopropane hydrochloride. A mixture of 2-acetyl-5-bromobenzo[b] furan (23.9 g, 0.1 mol), dimethylamine hydrochloride(8.15 g, 0.1 mol), paraformaldehyde (3.6 g) and 2 ml of 35% hydrochloric acid in 150 ml of ethanol was heated at reflux for 20 h (TLC followed). The solvent volume was reduced under reduced pressure to 50 ml and a mixture of acetone: ether (1:2) was added and the resultant solid was filtered, washed with ether and dried at 45° C. in a vacuum oven for 24 h to yield 23.0 g (69%), mp 185–187° C. dec. $^1$H NMR (DMSO-$d_6$): 8.07 (d, J=2.0 Hz, 1H), 7.91 (s, 1H), 7.70 (d, J=8.8 Hz, 1H), 7.66 (dd, J=2.0 Hz, J=8.8 Hz, 1H), 3.58 (t, J=7.2, 2H), 3.41(t, J=7.2, 2H),2.78(s,6H). $^{13}$CNMR(DMSO-$d_6$): 186.7, 153.7,152.2, 131.2, 128.8,126.0, 116.2, 114.3, 113.5, 51.0, 42.2, 33.3. The presence of small amount (ca. 5%) of the corresponding elimination product (vinyl ketone)

was apparent from the $^1$H NMR; the product was used directly in the next step with out further purification.

1-[(5-Bromobenzo [b]furan-2-yl]-4-(4-bromophenyl) butane-1,4-dione. A mixture of the above Mannich base (16.6 g, 0.05 mol), 3-benzyl-5(2-hydroxyethyl)-4-methyl thiazolium chloride catalyst(0.68, 0.0025 mol), triethylamine (15.15 g, 0.15 mol) and 4-bromobenzaldehyde (9.25 g, 0.05 mol) in 180 ml dioxane was heated at reflux for 12 h (under nitrogen). The solvent was removed under reduced pressure and the residue was treated with water. The resultant gummy material was extracted with 150 ml of chloroform. The organic layer was dried over $MgSO_4$ and the solvent was removed under reduced pressure. The residue was treated with EtOH:ether(1:1) the solid which remained was filtered, washed with ether and dried to yield 7.4 g(34%); mp 176–177° C.). $_1$H NMR (DMSO-$d_6$): 8.03 (dd, J=0.4 and 1.5 Hz, 1H), 7.91 (d, J=8.4 Hz, 2H), 7.82(d, J=0.4, 1H) 7.72 (d, J=8.4 Hz, 2H), 7.68 (d, J=8.8, 1H) 7.64 (dd, J=1.5 and 8.8 Hz, 1H), 3.40–3.45 (m, 2H), 3.37–3.33 (m, 2H). $^{13}$C NMR (DMSO-$d_6$): 197.3, 188.9, 153.5, 152.7, 135.2, 131.5, 130.7, 129.6, 128.8, 127.0, 125.7, 115.9, 114.1, 112.4, 32.3, 32.0. MS m/e 436 ($M^+$). Anal. Calcd for $C_{18}H_{12}Br_2O_3$ C, 49.57; H, 2.77. Found: C, 49.49; H, 2.74.

2-[(5-Bromobenzo[b]furan-2-yl]-5-(4-bromophenyl) furan. A solution of the above diketone (8.72 g, 0.02 mol) in 150 ml $CHCl_3$:MeOH(1:1) was saturated with HCl gas, stirred at room temperature for 4 h (TLC followed). The solvent was removed under reduced pressure and the residue was stirred with 200 ml 10% aqueous $NaHCO_3$, filtered, washed with water, dried and recrystallized from ether: $CH_2Cl_2$ (4: 1) to yield white solid 7.1 g(85%) mp 204–206° C. $^1$H NMR (DMSO-$d_6$): 7.86 (d, J=2.0, 1H)), 7.76 (d, J=8.4 Hz, 2H), 7.65(d, J=8.4, 2H) 7.58 (d, J=8.4 Hz, 1H), 7.45 (dd, J=2.0 and 8.4 Hz, 1H) 7.23 (s, 1H), 7.17 (d, J=4.0 Hz, 1H), 7.11(d, J=4.0 Hz, 1H). $^{13}$C NMR(DMSO-$d_6$): 152.9, 152.7, 148.0, 144.1, 131.6, 130.4, 128.4, 127.0, 125.5, 123.3, 120.9 115.5, 112.7, 111.2, 108.6, 101.1. MS m/e 436($M^+$). Anal. Calcd for $C_{18}H_{12}Br_2O_3$ C, 49.57; H, 2.77. Found: C, 49.49; H, 2.74.

2-[(5-Cyanobenzo [b]furan-2-yl]-5-(4-cyanophenyl) furan. A mixture of the above dibromo compound (8.36 g, 0.02 mol) and CuCN(5.34 g, 0.06 mol) in 60 ml of N-methyl-2-pyrolidinone was heated at reflux for 4 h (under nitrogen), cooled, diluted with water and stirred with 200 ml of 10% aqueous NaCN for 3 h. The solid was filtered, washed with water and dried. The crude product was dissolved in $CHCl_3$:MeOH(1:1) and chromatographed over neutral alumina to yield a pale yellow solid 4.35 g(70%), mp 247–248° C. $^1$H NMR (DMSO-$d_6$): 8.18 (d, J=1.6, 1H)), 7.98 (d, J=8.0 Hz, 2H), 7.88(d, J=8.0,2H) 7.81 (d, J=8.4 Hz, 1H), 7.73 (dd, J=1.6 and 8.4 Hz, 1H) 7.41 (s, 1H), 7.38 (d,1H, J=3.6 Hz), 7.21(d,1H, J=3.6 Hz). $^{13}$C NMR (DMSO-$d_6$): 155.6, 152.4, 148.4, 144.7,132.9, 132.6, 128.8, 128.3, 126.1, 124.1, 118.6, 118.3, 112.3, 111.9, 111.2, 106.4, 101.9. MS m/e 310($M^+$). Anal. Calcd for $C_{20}H_{10}N_2O_2$ C, 77.41; H, 3.25; N, 9.02. Found: C, 77.41; H, 3.26; N, 8.95.

2-[(5-Amidinobenzo[b]furan-2-yl]-5-(4-amidinophenyl) furan dihydrochloride. The above dicyano compound (3.1 g, 0.01 mol) in 70 ml of ethanol was saturated with dry HCl gas at 0–5° C. and then stirred at room temperature for 8 da (monitored by IR and TLC). Ether was added to the mixture and the yellow imidate ester dihydrochloride was filtered and washed with ether. The solid was dried at 50° C. in a vacuum for 24 h, to yield 4.3 g (93%). The solid was used directly in the next step without further purification.

A suspension of imidate ester dihydrochloride (1.43 g, 0.003 mol) in 20 ml of ethanol was saturated with ammonia gas, stirred for 24 h and the solvent was removed under reduced pressure. The solid was suspended in water and the pH was adjusted to 9 and the off-white solid was filtered. The solid was stirred in HCl saturated ethanol and the yellow salt was filtered and dried in a vacuum oven at 75° C. for 24 h to yield 0.7 g (68%) mp 320 dec. $_1$H NMR (DMSO-$d_6$/ $D_2$O): 8.20 (d, J=1.2, 1H)), 8.01 (d, J=8.0 Hz, 2H), 7.74(d, J=8.0, 2H) 7.82 (d, J=8.4 Hz, 1H), 7.78 (dd, J=1.2 and 8.4 Hz, 1H) 7.47 (s, 1H), 7.37 (d,1H, J=3.6 Hz), 7.20(d,1H, J=3.6 Hz). $^{13}$C NMR (DMSO-$d_6$): 165.7, 164.8, 156.7, 152.8, 148.6, 145.0, 134.0, 128.9, 128.7, 126.4, 124.9, 123.9, 123.3, 122.0, 112.1, 111.8, 111.2, 102.5. FABMS m/e 345($M_++1$). Anal. Calcd for $C_{20}H_{16}N_4O_2 \cdot 2HCl \cdot 0.5H_2O$: C, 56.36; H, 4.49; N, 13.14. Found: C, 56.73; H, 4.71; N, 12.71.

EXAMPLE 2

DNA Fingerprinting Studies

In order to characterize the DNA recognition properties of a series of analogs of furamidine (shown in FIG. 1), quantitative DNAaseI footprinting studies were conducted using of a number of derivatives with several different DNA sequences. Plasmid DNA restriction fragments were prepared and DNaseI footprinting experiments were conducted as described in C. Bailly, et al., *Biochemistry* 35, 1150 (1996) and C. Bailly et al., *Anti Cancer Drug Design* (in press, 1999).

Figure 2:
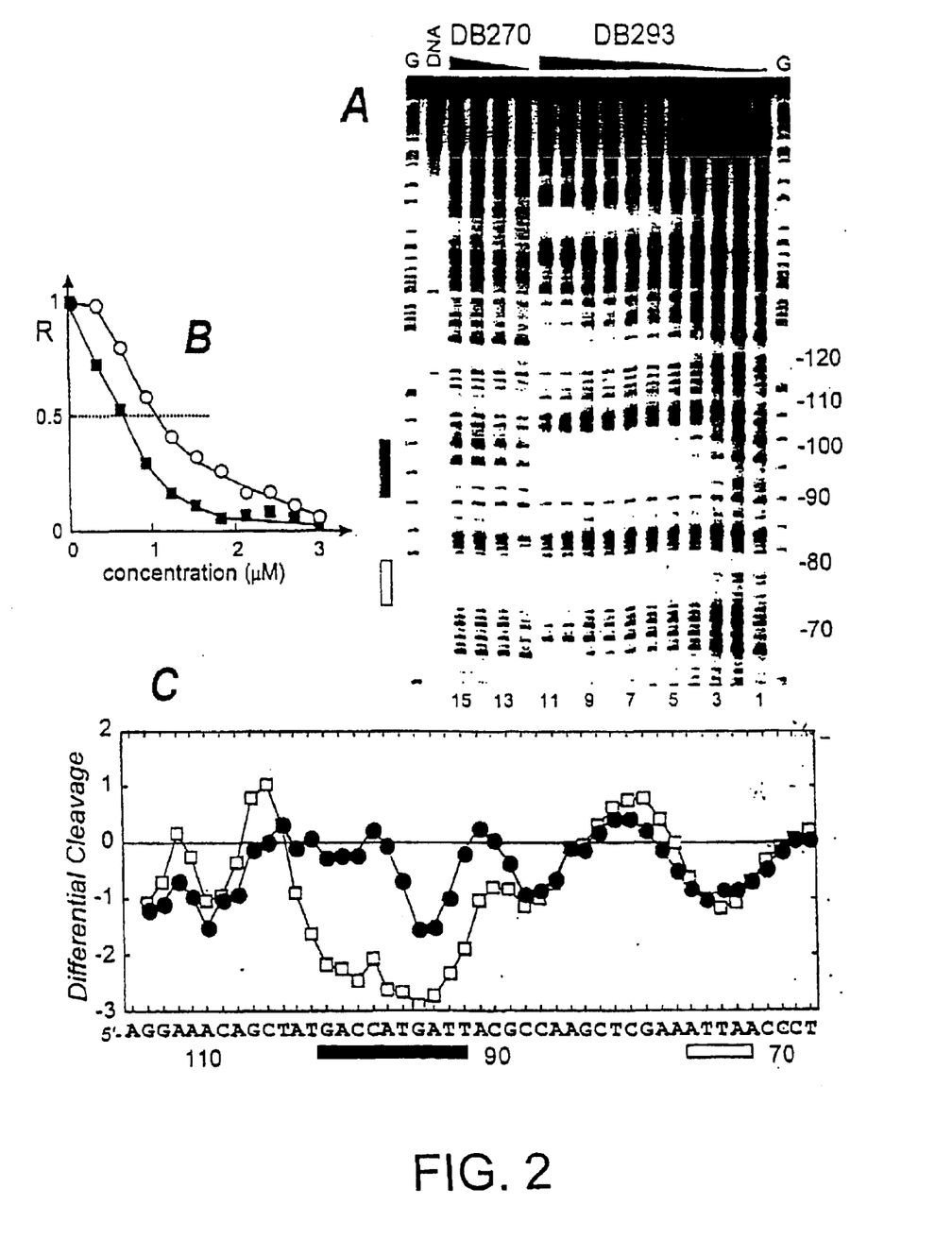
FIG. 2. illustrates the results of a quantitative DNase I footprinting titration experiment with the compound DB293 on the 265 bp DNA fragment as described herein. The EcoRI-PvuII restriction fragment from plasmid pBS was 3'-end labeled at the EcoRI site with [$\alpha$-$^{32}$P]dATP in the presence of AMV reverse transcriptase.

FIG. 2. illustrates the results of a quantitative DNase I footprinting titration experiment with the compound DB293 on a 265 bp DNA fragment as described herein. The EcoRI-PvuII restriction fragment from plasmid pBS was 3'-end labeled at the EcoRI site with [α-$^{32}$P]dATP in the presence of AMV reverse transcriptase. As illustrated in FIG. 2A, the products of the DNase I digestion were resolved on an 8% polyacrylamide gel containing 8M urea. Drug concentrations are (lanes 1–11) 0, 0.3, 0.6, 0.9, 1.2, 1.5, 1.8, 2.1, 2.4, 2.7, 3.0 μM for DB 293 and (lanes 12–15) 0, 1, 2 and 5 μM for DB270. Tracks labeled 'G' represent dimethylsulphate-piperidine markers specific for guanines. The track labeled DNA contained no drug and no enzyme. Numbers at the right side of the gel refer to the numbering scheme of the fragment. The rectangles on the left side refer to the positions of (open box) an AT-rich and (filled box) a GC-rich binding site for DB293. FIG. 2B is a graphical illustration of footprinting plots for the binding of DB293 to (open circles) the AT site 5'-AATTAA and (filled squares) the GC-rich site 5'-ACCATG. The relative band intensity R corresponds to the ratio $I_c/I_o$ where $I_c$ is the intensity of the band at the ligand concentration c and $I_o$ is the intensity of the same band in the absence of DB293. The differential cleavage plots shown in FIG. 2C compare the susceptibility of the DNA to cutting by DNase I in the presence of (filled circles) 5 μM DB270 or (open squares) 1.5 μM DB293. Deviation of points towards the lettered sequence (negative values) corresponds to a ligand-protected site and deviation away (positive values) represents enhanced cleavage. The vertical scale is in units of $\ln(f_a)-\ln(f_c)$, where $f_a$ is the fractional cleavage at any bond in the presence of the drug and $f_c$ is the fractional cleavage of the same bond in the control. The results are displayed on a logarithmic scale. The rectangles below the sequence show the positions of (open box) the AT binding site and (filled box) the GC-rich site.

Results with the symmetric compounds furamidine and the bisbenzimidazole DB270 are as expected for AT specific minor-groove binding agents and agree with observations on other furan derivatives and related compounds. With the asymmetrical compound DB293 (FIG. 1), however, the footprinting results present a number of surprises in the form of strong footprints in unexpected GC-rich regions, as shown in FIG. 2. In the 90–100 base region of the 265mer pBS fragment in FIG. 2, for example, DB293 gave a very strong footprint while DB270 and furamidine give negligible footprints. The most surprising feature of the footprint in this sequence region is its GC content relative to the AT rich sequences, where footprints are usually observed with minor-groove agents Quantitative analysis of the footprinting data reveals that the $C_{50}$ value, the drug concentration required for half-maximal footprinting, at the ATGA site is significantly lower than at the neighboring ATTA site, indicating that DB293 prefers the site including a GC base pair over the site containing only AT base pairs. The differential cleavage plots show that both DB270 and DB293 bind similarly to sites composed exclusively of AT base pairs (FIG. 2). Footprinting studies with several restriction fragments showed DB293, but not DB270, strongly binds to sites containing GC base pairs, such as ATGA, ACGA, and ATGT.

EXAMPLE 3

Thermal Melting Experiments

Figure 1:
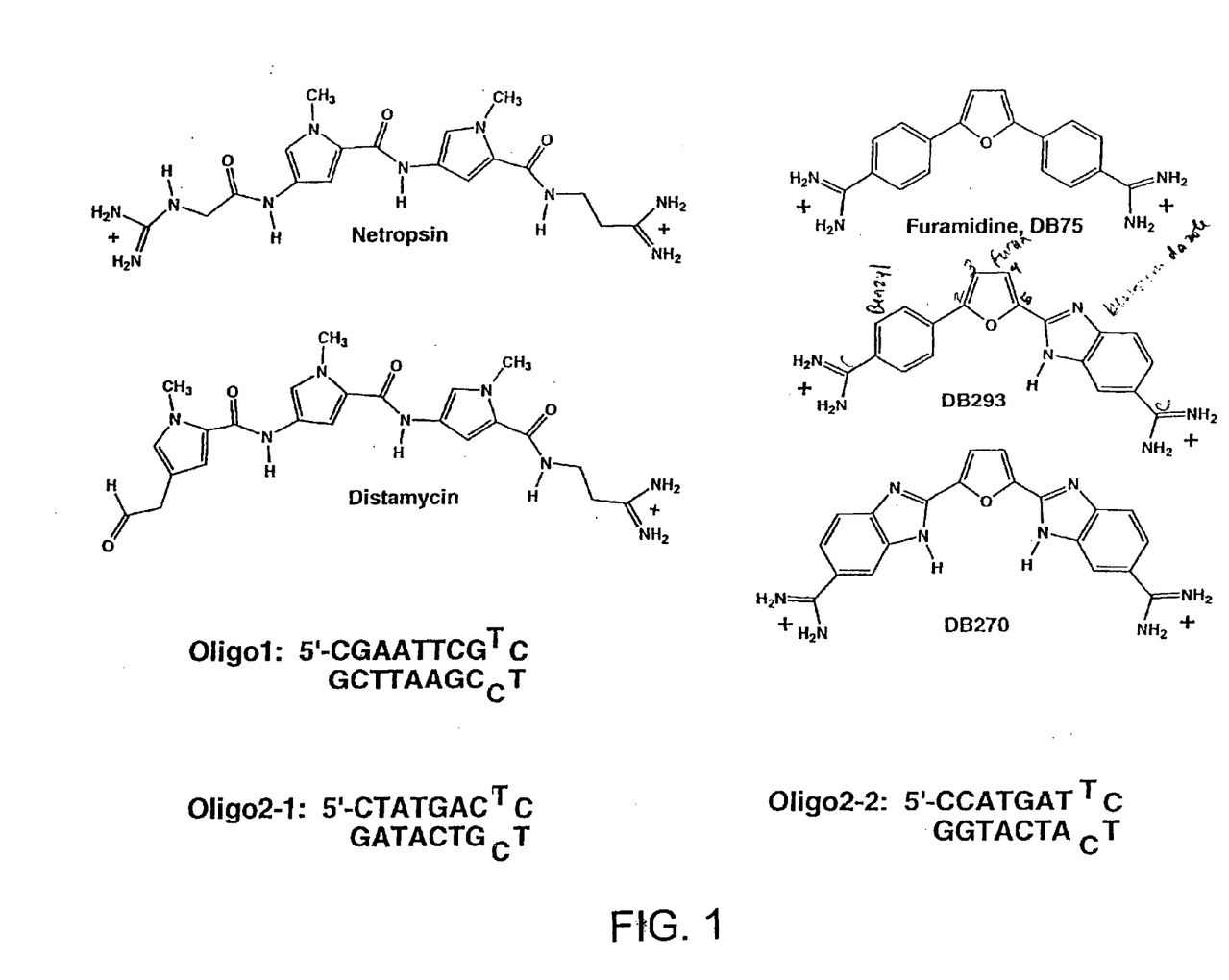

In order to investigate the complexes of these compounds in more detail with GC rich sequences, a hairpin duplex model containing the 93–104 base sequence region from the 265mer pBS restriction fragment was synthesized and is illustrated as oligo2 in FIG. 1. Oligo 1 (also shown in FIG. 1) with the AATT sequence that has been used in the analysis of a large number of minor-groove agents provides a reference.

Thermal melting experiments were conducted with a Cary 4 spectrophotometer interfaced to a microcomputer. A thermistor fixed into a reference cuvette was used to monitor the temperature. The oligomers were added to 1 mL of buffer (0.01 M MES and 0.001M EDTA) in 1 cm path length reduced volume quartz cells, and the concentration was determined by measuring the absorbance at 260 nm. Experiments were generally conducted at a concentration of $2 \times 10^{-6}$ M for hairpin oligo2, and $3 \times 10_{-6}$ M for hairpin oligo2-1. Tm experiments for the complexes were conducted as a function of ratio.

Figure 5:
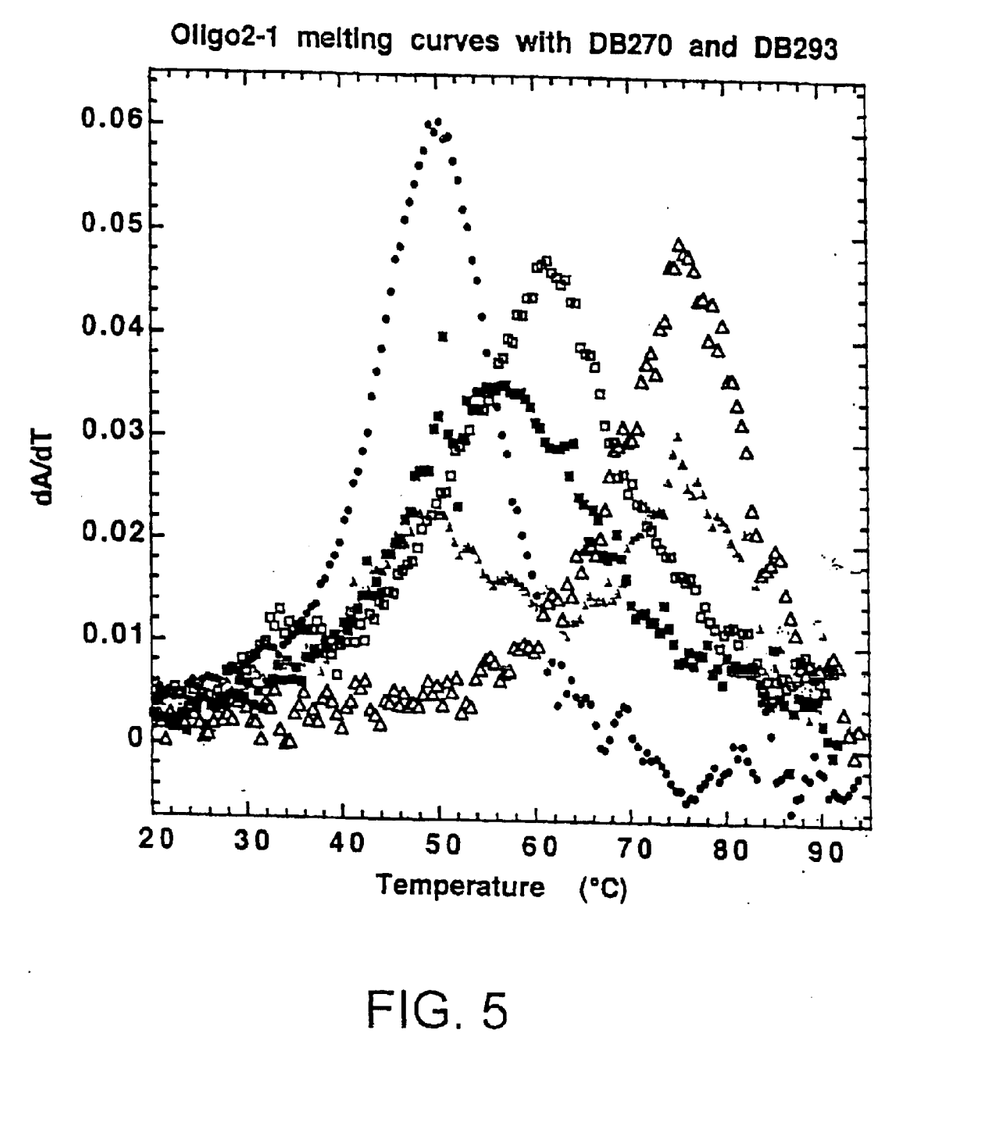
FIG. 5 illustrates Tm curves as a function of ratio for complexes of DB270 and DB293 with oligo 2-1. Closed circles indicate free DNA; closed triangles and open triangles indicate DB293 at 1:1 and 2:1 ratios, respectively, and closed squares and open squares indicate DB270 at 1:1 and 2:1 ratios, respectively.
Figure 6:
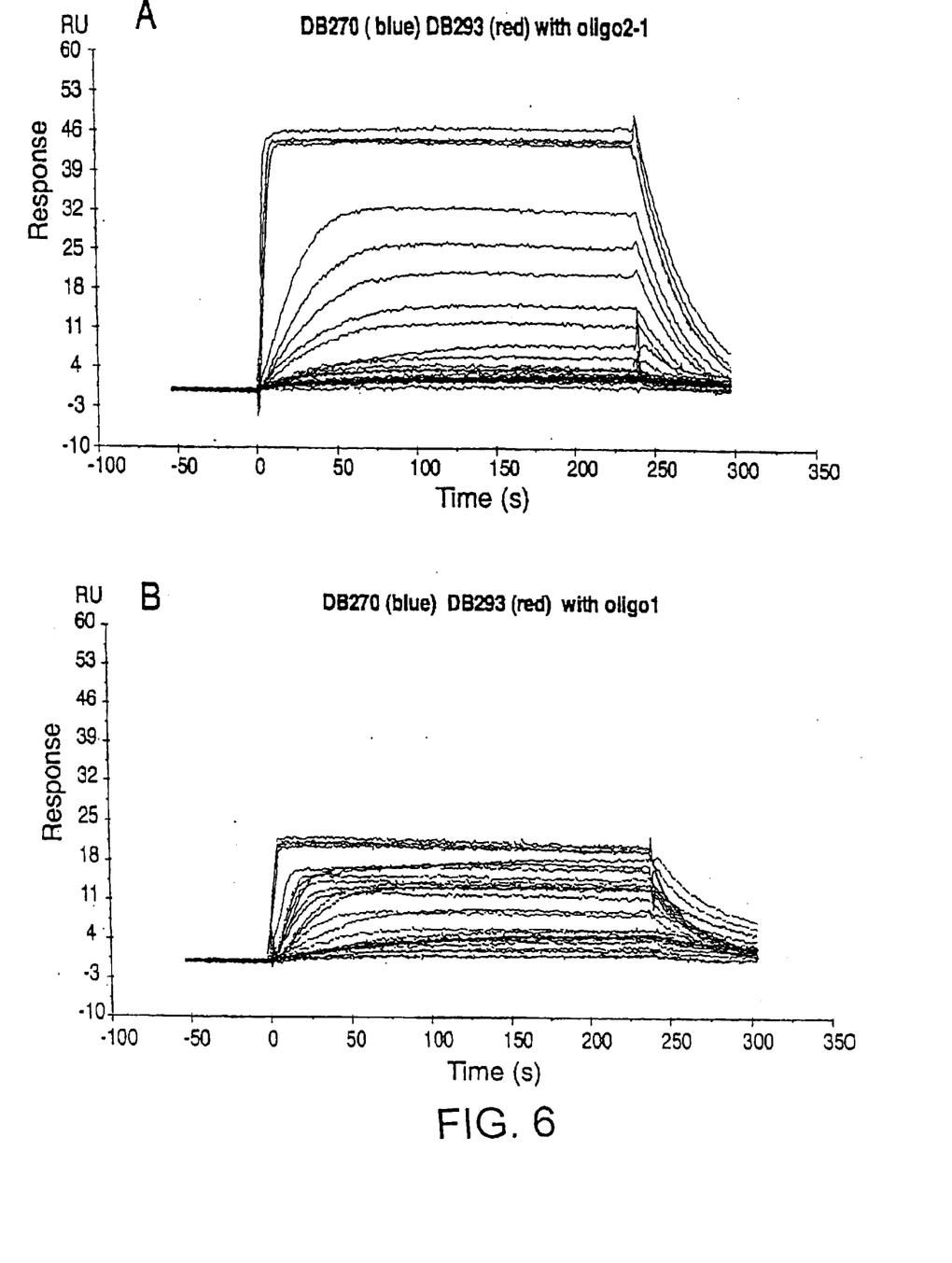
FIG. 6 sets forth sensorgrams for binding of DB270 and DB 293 to (top, A) oligo2-1 and (bottom, B) oligo 1. Drug concentrations range from 1 nM to 1 μM.

Tm determinations of oligo2 on titration with DB293 gave up to a 30° C. increase in Tm and did not level off until a ratio of 4:1 DB293:hairpin duplex had been reached. The high ratio of DB293 to oligomer duplex was surprising for a duplex of only 13 base pairs. In order to better understand the nature of the complex, divided oligo2 was divided into two similar hairpin duplexes, oligo2-1 and oligo2-2 (FIG. 1). As an illustration of the results obtained, derivative Tm curves of DB270 and DB293 complexes with oligo2-1 are shown in FIG. 5. The DB293 complex has a biphasic melting curve at a 1:1 ratio with a high temperature phase and a low temperature phase near the Tm of the free hairpin duplex. At a 2:1 ratio, the low temperature phase disappears and only the high temperature transition is present. Melting curves of DB270 and furamidine complexes with oligo2-1 have single transitions at 1:1 and 2:1 ratios with melting temperatures below the DB293 value. As with the footprinting experiments, these results illustrate the dramatic differences in DNA interactions between the symmetric compounds relative to the unsymmetric DB293. In addition, the Tm ratio results suggest that the unusual DNA recognition properties of DB293 are due to formation of 2:1 complexes with oligo2-1 and 2-2, and a 4:1 complex with oligo2. Such dimer complexes could also explain the unexpected footprinting behavior of DB293, however, based on the +2 charge of DB293, dimer complexes are not expected.

EXAMPLE 4

Surface Plasmon Resonance Experiments

To pursue the comparative quantitative analysis of these compounds with DNA in more detail by using surface plasmon resonance, 5'-biotin labeled analogs of oligo2-1 and 2-2 were immobilized on a BIAcore four-channel streptavidine-coated sensor chip as follows: Immobilization of DNA and surface plasmon resonance (SPR) binding studies: 5'-biotin labeled hairpins were purchased with HPLC purification (Midland Co). Samples of the DNA in MES10 buffer (0.1M MES and 0.001M EDTA, with 0.1M NaCl) at 50 nM concentration were applied to a BIAcore SA (streptavidin) chip by direct flow at 5 µl/min in a BIAcore 2000 SPR instrument. Nearly the same amount of oligo1, oligo2-1 and oligo2-2 were immobilized on the surface of the SA chip. Steady state analysis was performed with multiple injections of different concentrations of each compound over the SA surface at a flow rate of 20 µl/min, at 25° C.

Figure 3:
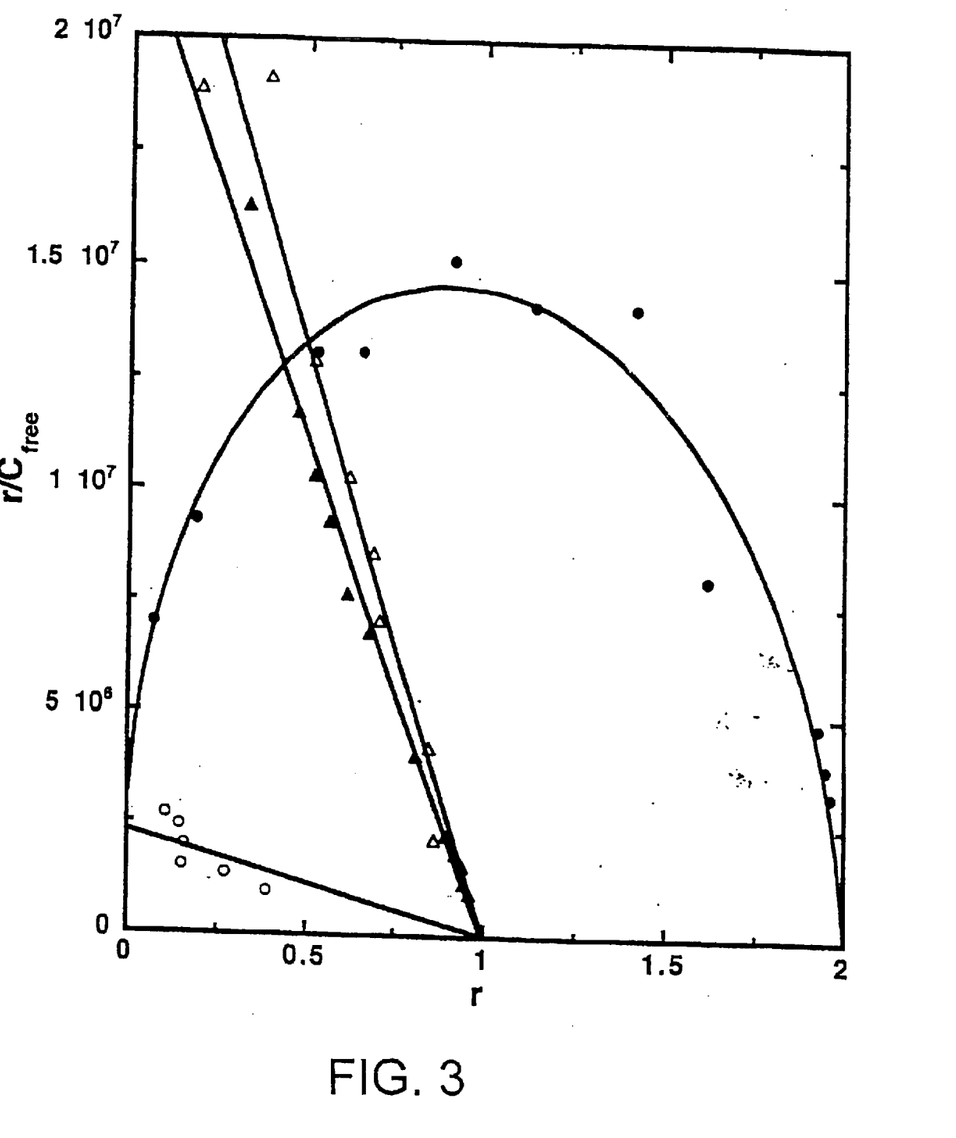
FIG. 3 sets forth Scatchard plots of the results for binding of DB293 and DB270 to oligo1 and oligo2-1 along with best fit binding curves are shown: closed triangles and open triangles are for DB293 and DB270, respectively, binding to oligo1. Closed circles and open circles are for DB293 and DB270 binding to oligo2-1, respectively Because of the weak binding of DB270 to oligo2-1, the results were fit with the assumption of a single DB270 binding to the duplex. Sensorgrams with the data for this plot are shown in FIG. 6.

Oligo1 was immobilized as a control sequence and one flow cell was left as an unmodified reference. Binding results from the SPR experiments were fit with either a single site model ($K_2=0$) or with a two site model: $r = (K_1 * C_{free} + 2 * K_1 * K_2 * C_{free}^2)/(1 + K_1 * C_{free} + 2 * K_1 * K_2 * C_{free}^2)$ where r represents the moles of bound compound per mole of DNA hairpin duplex, $K_1$ and $K_2$ are macroscopic binding constants, and $C_{free}$ is the free compound concentration in equilibrium with the complex. The free compound is fixed by the concentration in the flow solution. Binding of all of the furan derivatives to oligo 1 is best fit by the single site model, while binding of DB293 to oligo2-1 and 2-2 requires the two site model and $K_2$ is found to be much greater than $K_1$ as expected for interactions with very large positive cooperativity. Oligos 1 and 2-1 are shown in FIG. 3 to illustrate the differences.

The binding of all of the furan compounds to oligo1 is similar and saturation is reached at a 1:1 ratio, as expected from results with a number of minor-groove binding cations with DNA duplexes containing an AATT sequence. The results for DB293 binding to oligo2-1 and 2-2 are, however, dramatically different from results with the symmetric compounds, and are dramatically different from the results obtained with oligo1 and DB293. Scatchard plots for binding of DB293 and DB270 are set forth in FIG. 3.

As in footprinting experiments with AT sites (FIG. 2), DB270 and DB293 bind in a very similar manner to oligo1 with linear Scatchard plots indicating one type of strong binding site that binds a single molecule of DB270 or DB293 with binding constants of $2.3$–$2.6 \times 10^7$. Binding of DB270 to oligo2-1 is at least a factor of ten weaker than its binding to oligo1 and probably represents its interaction at the TAT sequence in the oligomer that is too short to form a very strong minor-groove complex. As shown in FIG. 3, however, binding of DB293 with oligo2-1 is highly cooperative and saturates at two molecules of DB293 per oligo2-1 hairpin duplex. Fitting of the binding results to a two site model to determine the macroscopic binding constants gave a binding constant ($K_1$) of $2.8 \times 10^6$ for initial binding and a $K_2$ of $7.3 \times 10^7$ for binding to the second site after the first site is filled. Very similar results are obtained for binding of DB293 to oligo2-2. The similarity of binding constants for DB270 and the first molecule of DB293 binding to oligo2-1 and 2-2 suggests that these are similar processes. The dramatic difference occurs when the second molecule of DB293 binds cooperatively with a $K_2$ that is over 25 times larger than for binding of DB270 and the first molecule of DB293 ($K_1$) to the oligomers. These results strongly suggest that the unusual footprinting pattern observed with DB293 is due to formation of a highly cooperative 2:1 complex in specific DNA sequences. The close analogs, furamidine and DB270, do not bind strongly or footprint in these DNA sequences. Since all three furan compounds are dications, it is clearly structure, and not charge, that prevents the symmetric derivatives from forming the dimer complex.

EXAMPLE 5

Structural Studies of Furan Derivatives

Structural studies of a number of furan derivatives with oligomers containing the AATT sequence of oligo1, including X-ray structures of furamidine and alkyl derivatives, have clearly demonstrated a 1:1 classical minor-groove binding complex in which the amidine groups interact with the edges of A and T bases at the floor of the groove in the AATT site. See C. A. Laughton, *Biochemistry* 35, 5655 (1996) and S. Neidle, *Biopolymers* 44, 105 (1997). This is the type of complex expected from the experimental results of the furans of FIG. 1 with oligo1. In order to characterize the 2:1 complex of DB293, NMR studies of the DB293-oligo2-1 complex were initiated. All NMR spectra were acquired with a Varian Unity Plus 600 MHz spectrometer. Typical conditions for the collection of spectra in $D_2O$: 2 s relaxation delay, 0.6 mL sample in a 5 mm NMR tube, and 1.0 Hz line broadening before Fourier transformation. Two-dimensional experiments were obtained with a spectral width of 6000 Hz in both dimensions with 2048 complex data points in the t2 dimension and 512 points in the t1 dimension, while 1D spectra were collected with a spectral width of 6000 Hz and 32K data points.

Figure 4:
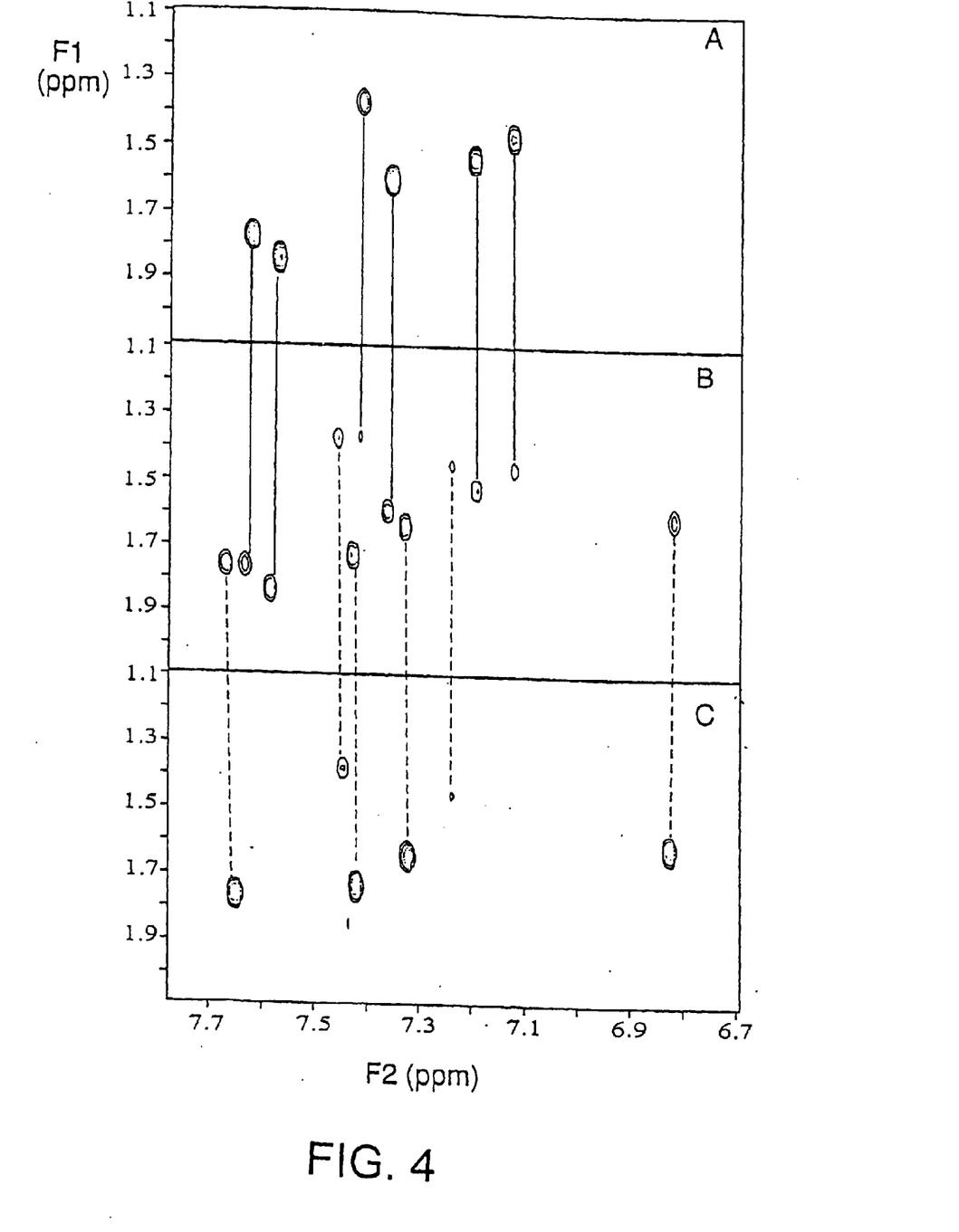
FIG. 4. is a two-dimensional COSY spectra of the TH6-TCH3 spectral region shown for (top, A) free DNA; (middle, B) a 1:1 ratio sample of DB293 to oligo2-1; and (bottom, C) a 2:1 ratio. Signals for the free DNA and for the 2:1 complex in the 1:1 ratio sample are indicated by connecting lines to the top and bottom spectra.

In proton NMR titrations of the oligomer duplex with DB293 only two DNA species are detected at a 1:1 molar ratio. The two species are clearly illustrated with 2D COSY spectra in FIG. 4 for the aromatic to thymine methyl NMR spectral region. The free DNA has six well resolved TH6-TCH$_3$ cross peaks as expected for the six T residues in the oligomer. In the 1:1 ratio complex there are 12 cross peaks as expected for two species in slow exchange, and one species has the same chemical shifts as the free DNA. At the 2:1 ratio the free DNA signals disappear and the signals for the 2:1 complex double in intensity. The 2:1 complex and the free DNA are the only species observed in the 1:1 ratio COSY spectrum (FIG. 4) in agreement with the high cooperativity observed in the binding experiments. No intermediate signals for a 1:1 complex can be detected in any experiments throughout the titration of oligo2-1 with DB293, and the two species that we observe at the 1:1 ratio are free oligomer and the 2:1 complex. In 2D NOESY analysis strong signals are obtained for the C H5–H6 interactions, and again only signals for free DNA and the 2:1 complex are detected (not shown). In contrast, two sets of cross peaks are detected for DB293 in the oligo2-1 complex as expected for two distinct bound molecules in slow exchange. Cross peaks between the two DB293 molecules and from DB293 to DNA minor-groove protons clearly show that the compound binds in the minor groove as an antiparallel dimer and makes contact with both DNA strands. Strong crosspeaks from the two bound DB293 molecules to DNA base pairs from T4.A15 to C7.G12 are observed and these interactions place the dimer in the ATGA sequence that is common to both oligo2-1 and 2-2.

From these results it is clear that all three furan derivatives of FIG. 1 bind to the AATT sequence in oligo1 as classical minor-groove monomer complexes. The symmetric compounds such as DB270 and furamidine do not form the dimer species in a DNA complex and, therefore, do not bind to DNA sequences that do not have classical AT minor-groove binding sites. DB293 forms an antiparallel, stacked dimer in complex with DNA sites that contain ATGA and probably other sequences. The dimer complex provides a new motif for understanding and design of compounds that can recognize DNA sequences containing both AT and GC base pairs. The results presented herein show that the binding of aromatic dications to mixed DNA sequences is exquisitely sensitive to compound structure and DNA sequence. Although Applicants do not wish to be bound by any theory of the invention, it appears that the reasons for the cooperative formation of the DB293 dimer complex are encoded in the interactions between a specific DNA sequence and the orientation of chemical groups in the dimer. Favorable stacking of DB293 to give a dimer in the context of the anionic DNA minor groove can also contribute to the 2:1 complex.

The foregoing is illustrative of the present invention and is not to be construed as limiting thereof. The invention is defined by the following claims, with equivalents of the claims to be included therein.

That which is claimed is:

1. A compound of Formula I:

wherein:

X is selected from the group consisting of O and S;

Y is CH;

A is N;

B is selected from the group consisting of NH and O, provided that when X is O and A is N, B is not NH;

$R_1$ is selected from the group consisting of H, loweralkyl, halogen, oxyalkyl, oxyaryl, and oxyarylakyl;

$R_2$ and $R_9$ are each independently selected from the group consisting of H, hydroxy, lower alkyl, cycloalkyl, aryl, alkylaryl, alkoxyalkyl, hydroxycycloalkyl, alkoxycycloalkoxy, hydroxyalkyl, aminoalkyl and alkylaminoalkyl; and $R_3$, $R_4$, $R_{13}$ and $R_{14}$ are each independently selected from the group consisting of H, lower alkyl, alkoxyalkyl, cycloalkyl, aryl, alkylaryl, hydroxyalkyl, aminoalkyl, and alkylaminoalkyl, or $R_3$ and $R_4$ together or $R_{13}$ and $R_{14}$ together represent a $C_2$ to $C_{10}$ alkyl, hydroxyalkyl, or alkylene, or $R_3$ and $R_4$ together or $R_{13}$ and $R_{14}$ together are:

wherein n is a number from 1 to 3, and $R_{10}$ is H or —$CONHR_{11}NR_{15}R_{16}$, wherein $R_{11}$ is lower alkyl and $R_{15}$ and $R_{16}$ are each independently selected from the group consisting of H and lower alkyl;

L is:

wherein $R_5$, $R_6$, $R_7$, and $R_8$ are each individually selected from the group consisting of H, alkyl, halo, aryl, arylalkyl, aminoalkyl, aminoaryl, oxoalkyl, oxoaryl, and oxoarylalkyl; and wherein said compound of Formula I binds the minor groove of DNA as a dimer.

2. A method of binding mixed sequence DNA comprising contacting a sample DNA with a compound of Formula (I):

wherein:

X is selected from the group consisting of O and S;

Y is CH;

A is N;

B is selected from the group consisting of NH and O provided that when X is O and A is N, B, is not NH;

$R_1$ is selected from the group consisting of H, loweralkyl, halogen, oxyalkyl, oxyaryl; and oxyarylakyl;

$R_2$ and $R_9$ are each independently selected from the group consisting of H, hydroxy, lower alkyl, cycloalkyl, aryl, alkylaryl, alkoxyalkyl, hydroxycycloalkyl, alkoxycycloalkoxy, hydroxyalkyl, aminoalkyl and alkylaminoalkyl; and $R_3$, $R_4$, $R_{13}$ and $R_{14}$ are each independently selected from the group consisting of H, lower alkyl, alkoxyalkyl, cycloalkyl, aryl, alkylaryl, hydroxyalkyl, aminoalkyl, and alkylaminoalkyl, or $R_3$ and $R_4$ together or $R_{13}$ and $R_{14}$ together represent a $C_2$ to $C_{10}$ alkyl, hydroxyalkyl, or alkylene, or $R_3$ and $R_4$ together or $R_{13}$ and $R_{14}$ together are:

wherein n is a number from 1 to 3, and $R_{10}$ is H or —$CONHR_{11}NR_{15}R_{16}$, wherein $R_{11}$ is lower alkyl and $R_{15}$ and $R_{16}$ are each independently selected from the group consisting of H and lower alkyl;

L is:

wherein $R_5$, $R_6$, $R_7$, and $R_8$ are each individually selected from the group consisting of H, alkyl, halo, aryl, arylalkyl, aminoalkyl, aminoaryl, oxoalkyl, oxoaryl, and oxoarylalkyl; wherein said compound of Formula I binds the minor groove of DNA as a dimer.

3. A method of detecting mixed sequence DNA comprising contacting a sample of DNA with a fluorescent compound of Formula (I):

(I)

wherein:
X is selected from the group consisting of O and S;
Y is CH;
A is N;
B is selected from the group consisting of NH and O, provided that when X is O and A is N, B is not NH;
$R_1$ is selected from the group consisting of H, loweralkyl, halogen, oxyalkyl, oxyaryl, and oxyarylakyl;
$R_2$ and $R_9$ are each independently selected from the group consisting of H, hydroxy, lower alkyl, cycloalkyl, aryl, alkylaryl, alkoxyalkyl, hydroxycycloalkyl, alkoxycycloalkoxy, hydroxyalkyl, aminoalkyl and alkylaminoalkyl; and
$R_3$, $R_4$, $R_{13}$ and $R_{14}$ are each independently selected from the group consisting of H, lower alkyl, alkoxyalkyl, cycloalkyl, aryl, alkylaryl, hydroxyalkyl, aminoalkyl, and alkylaminoalkyl, or $R_3$ and $R_4$ together or $R_{13}$ and $R_{14}$ together represent a $C_2$ to $C_{10}$ alkyl, hydroxyalkyl, or alkylene, or $R_3$ and $R_4$ together or $R_{13}$ and $R_{14}$ together are:

wherein n is a number from 1 to 3, and $R_{10}$ is H or —$CONHR_{11}NR_{15}R_{16}$, wherein $R_{11}$ is lower alkyl and $R_{15}$ and $R_{16}$ are each independently selected from the group consisting of H and lower alkyl;

L is:

wherein $R_5$, $R_6$, $R_7$, and $R_8$ are each individually selected from the group consisting of H, alkyl, halo, aryl, arylalkyl, aminoalkyl, aminoaryl, oxoalkyl, oxoaryl, and oxoarylalkyl; and wherein said compound of Formula I binds the minor groove of DNA as a dimer;
and then observing fluorescence in the sample, the observation of fluorescence indicating the compound of Formula I has bound to a sequence of DNA.

4. A pharmaceutical formulation comprising a compound of Formula I:

(I)

wherein:
X is selected from the group consisting of O and S;
Y is CH;
A is N;
B is selected from the group consisting of NH and O, provided that when X is O and A is N, B is not NH;
$R_1$ is selected from the group consisting of H, loweralkyl, halogen, oxyalkyl, oxyaryl, and oxyarylakyl;
$R_2$ and $R_9$ are each independently selected from the group consisting of H, hydroxy, lower alkyl, cycloalkyl, aryl, alkylaryl, alkoxyalkyl, hydroxycycloalkyl, alkoxycycloalkoxy, hydroxyalkyl, aminoalkyl and alkylaminoalkyl; and
$R_3$, $R_4$, $R_{13}$ and $R_{14}$ are each independently selected from the group consisting of H, lower alkyl, alkoxyalkyl, cycloalkyl, aryl, alkylaryl, hydroxyalkyl, aminoalkyl, and alkylaminoalkyl, or $R_3$ and $R_4$ together or $R_{13}$ and $R_{14}$ together represent a $C_2$ to $C_{10}$ alkyl, hydroxyalkyl, or alkylene, or $R_3$ and $R_4$ together or $R_{13}$ and $R_{14}$ together are:

wherein n is a number from 1 to 3, and $R_{10}$ is H or —$CONHR_{11}NR_{15}R_{16}$, wherein $R_{11}$ is lower alkyl and $R_{15}$ and $R_{16}$ are each independently selected from the group consisting of H and lower alkyl;

L is:

wherein $R_5$, $R_6$, $R_7$, and $R_8$ are each individually selected from the group consisting of H, alkyl, halo, aryl, arylalkyl, aminoalkyl, aminoaryl, oxoalkyl, oxoaryl, and oxoarylalkyl;
in a pharmaceutically acceptable carrier.

* * * * *